US009844490B2

(12) United States Patent
Ewing

(10) Patent No.: US 9,844,490 B2
(45) Date of Patent: Dec. 19, 2017

(54) DEVICE AND METHOD FOR ADMINISTERING MEDICINE

(71) Applicant: Dolores R. Ewing, Canton, OH (US)

(72) Inventor: Dolores R. Ewing, Canton, OH (US)

( * ) Notice: Subject to any disclaimer, the term of this patent is extended or adjusted under 35 U.S.C. 154(b) by 349 days.

(21) Appl. No.: 14/858,286

(22) Filed: Sep. 18, 2015

(65) Prior Publication Data

US 2016/0058671 A1 Mar. 3, 2016

Related U.S. Application Data

(63) Continuation of application No. 13/648,627, filed on Oct. 10, 2012, now abandoned.

(60) Provisional application No. 61/546,015, filed on Oct. 11, 2011.

(51) Int. Cl.
*A61M 31/00* (2006.01)
*A61J 7/00* (2006.01)

(52) U.S. Cl.
CPC ........... *A61J 7/0061* (2013.01); *A61J 7/0023* (2013.01)

(58) Field of Classification Search
CPC .......... A61J 7/00; A61J 7/0015; A61J 7/0023; A61J 7/0046; A61J 7/0053; A61J 7/0061; A61J 7/0076; A61J 1/03; A61J 3/005; A61J 3/07; B65D 84/32; B65D 84/3205; B65D 84/3211; B65D 84/3255
USPC ............ 604/514; 30/141, 324, 125; 426/115
See application file for complete search history.

(56) References Cited

U.S. PATENT DOCUMENTS 3,618,751 A * 11/1971 Rich .................... B65D 75/326 206/219
5,203,459 A * 4/1993 Wade .................. A47G 21/004 206/572
2013/0047446 A1* 2/2013 Leffler ................. A61J 7/0023 30/326

* cited by examiner

*Primary Examiner* — Kevin C Sirmons
*Assistant Examiner* — Leah Swanson
(74) *Attorney, Agent, or Firm* — Zollinger & Burleson Ltd.

(57) ABSTRACT

A device for administering medicine to a person includes a housing that supports an edible carrier. An element is disposed within the edible carrier for forming a recess within the edible carrier when the element and edible carrier are separated. The method includes the steps of forming the recess within the edible carrier, placing medicine within the recess, and administering the edible carrier and medicine combination to the recipient. The edible carrier provides lubrication and a pleasant taste to the person receiving the medicine. The housing may be in the form a spoon with the edible carrier sealed to the spoon.

20 Claims, 4 Drawing Sheets

DEVICE AND METHOD FOR ADMINISTERING MEDICINE

CROSS REFERENCE TO RELATED APPLICATIONS

This application is a continuation application that claims priority to U.S. patent application Ser. No. 13/648,627 filed Oct. 10, 2012, which claims the benefit of U.S. Provisional Patent Application Ser. No. 61/546,015 filed Oct. 11, 2011; the disclosures of both are incorporated herein by reference.

BACKGROUND OF THE DISCLOSURE

1. Technical Field

The disclosure generally relates to devices and methods for administering medicine. Specifically, the disclosure relates to a device for forming a recess in an edible carrier wherein medicine is placed in the recess and the edible carrier combined with the medicine are delivered to the person who needs the medicine. The device is used to help adults and children who have difficulties swallowing pills and capsules 2. Background Information Many adults and children have difficulties swallowing pills and capsules. This problem is of special concern in nursing homes and other health care facilities where a limited number of professionals have the responsibility to administer medicine to a large number of people. A single patient may need to take multiple prescriptions each day at different times. In this setting, repeated small delays in administering each item of medicine combine to significantly reduce the efficiency of the facility. Some patients with dry mouths or dry throats can generate a large delay in medicine delivery. Just a few large delays each day creates a significant impact on the efficiency of the facility. In an exemplary nursing facility of 100 residents taking medicine three times per day, a five minute delay in 50 percent of the medicine deliveries consumes over twelve hours of nursing time per day. This cost of medicine deliver is enlarged as more and more ailments are treated through prescriptions and when the nurse administering the medicine must ensure the resident has taken the medicine. The same costs are seen in hospitals. These industries thus desire an efficient mechanism and method for administering medicine to patients who have difficulties with swallowing pills in the traditional manner.

SUMMARY OF THE DISCLOSURE

The disclosure provides a plurality of different devices and different methods for administering medicine to a recipient.

In general, the device includes a housing that supports an edible carrier. An element is disposed within the edible carrier for forming a recess within the edible carrier when the element and edible carrier are separated. The method includes the steps of forming the recess within the edible carrier, placing medicine within the recess, and administering the edible carrier and medicine combination to the recipient. The method includes the steps of either adding the medicine to the edible carrier when the edible carrier is held within the housing or after the edible carrier is removed from the housing.

One exemplary configuration of the disclosure provides a housing that includes a base that holds the edible carrier and a cover that is releasably connected to the base. A probe element extends through the cover into the edible carrier. The portion of the probe element disposed within the base is substantially surrounded by the edible carrier. The edible carrier may be an edible gelatinous substance made from gelatin, water, and optionally sweetener, flavoring, and/or coloring. The user twists the probe element about its longitudinal axis to break any connection between the edible carrier and the probe element. The user may then pull the probe element straight out of the housing along the longitudinal axis of the probe element to define a recess in the edible carrier. The user then removes the cover and adds the medicine into the recess such that the medicine is substantially encapsulated by the material of the edible carrier. The user then squeezes the edible carrier from the base into a spoon or the recipient's hand wherein it can be placed on the user's tongue and then swallowed. The opening of the recess in the edible carrier should be directed towards the front of the recipient's mouth when the edible carrier is placed on the tongue. The edible carrier may be configured to have a pleasant taste and provides lubrication for the medicine.

Another exemplary configuration of the disclosure provides a housing that includes at least first and second portions that surround an edible carrier. A probe element is connected to the second portion of the housing such that when the second portion of the housing is removed from the first portion of the housing, the probe element is pulled from the edible carrier to define a recess within the edible carrier. The user may then insert medicine into the recess and administer the edible carrier to the recipient.

A further exemplary configuration of the disclosure provides a housing in the form of a spoon such that the housing itself may be used to administer the edible carrier and medicine to the recipient. The housing may thus include an elongated handle. The handle may include a recess or slot that helps the user load the medicine into the edible carrier.

The disclosure provides a housing member for the edible carrier that is deformable or crushable to assist the user in removing the edible carrier from the housing. The housing may be coated with a release layer that helps the edible carrier release from the housing.

The disclosure also provides a housing that carries the element such that the recess is formed in the edible carrier when the edible carrier is removed from the housing.

The disclosure provides a housing having a removable portion that is connected to an element that forms a recess within an edible carrier when the removable portion is removed from the housing. The removable portion may be a lid, a container half, or a peelable seal.

The edible carrier may be a traditional gelatin dessert composition. Alternatively, the edible carrier may be configured to be stable at room temperature for long periods of time. The edible carrier may be provided in different colors and favors. The edible carrier may be provided in different edible compositions.

The disclosure provides that a plurality of the devices may be connected and provided to the users in sheets, trays or rolls. The individual devices may be numbered with times, dates, names, room numbers, patient identification numbers, or consecutive numbering such that the user may conveniently use the devices with a plurality of recipients or so that a single recipient may track when the medicine has been taken. For example, the connected devices may be provided in an array of seven by three wherein the recipient needs to take medicine three times per day each day of the week.

DETAILED DESCRIPTION OF THE DISCLOSURE

Figure 1:
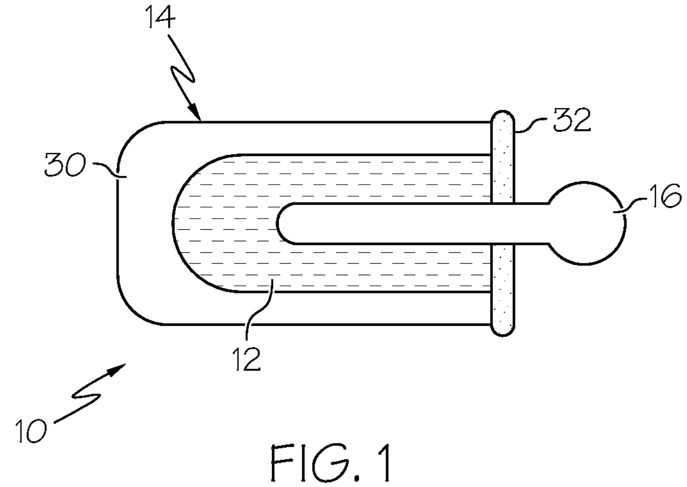
FIG. 1 is a side view of a first exemplary configuration of the device for administering medicine to a recipient.

The exemplary device configurations depicted in the accompanying drawings are generally indicated by the reference numeral 10. Each device 10 is used to provide an edible carrier 12 that is used to administer medicine to a recipient. The medicine 20 used with edible carrier 12 is a single or a plurality of dry pills, a single or a plurality of caplets, a single or a plurality of capsules, a single or a plurality of gel tabs, a powdered dose, or essentially any other form of medicine that may be placed in another carrier. The disclosure also provides methods for administering medicine to the recipient by using edible carrier 12 and methods of using device 10.

Each configuration of device 10 includes a housing 14 that supports edible carrier 12 in a manner that allows edible carrier 12 to be readily removed from housing 14. Housing 14 is provided in different shapes and sizes including a spoon-shaped housing and a pocket-shaped housing. At least a portion of an element 16 is disposed within edible carrier 12 for forming a recess 18 within edible carrier 12 when element 16 and edible carrier 12 are separated. The method includes the steps of forming a recess 18 within edible carrier 12, placing medicine 20 within recess 18, and administering edible carrier 12 and medicine 20 combination to the recipient. The method includes the steps of either adding medicine 20 to edible carrier 12 when edible carrier 12 is held within or on housing 14 or after edible carrier 12 is removed from housing 14.

Edible carrier 12 is formed from an edible material that is easy to swallow and has a self-supporting body capable of defining recess 18 and maintaining its shape about medicine 20 for long enough for medicine 20 to be swallowed by the recipient. Edible carrier 12 may be provided in the form of an edible gelatinous dessert substance made from gelatin, water, and optionally sweetener, flavoring, and/or coloring. Edible carrier 12 may be formed a variety of the products sold by Kraft Foods Global Brands LLC under the Federally-registered trademark JELL-O®. Edible carrier 12 may be a traditional gelatin-based dessert composition. The amount of water used to form carrier 12 partially controls the density of the carrier. Edible carrier 12 may be configured to be stable at room temperature for long periods of time. Edible carrier 12 may be provided in different colors and favors. Edible carrier 12 also may be provided in compositions that are not gelatin-based such as an edible polymer-based substance. Edible carrier 12 may be configured to have a pleasant taste and provides lubrication for assisting the recipient in swallowing medicine 20.

Figure 2:
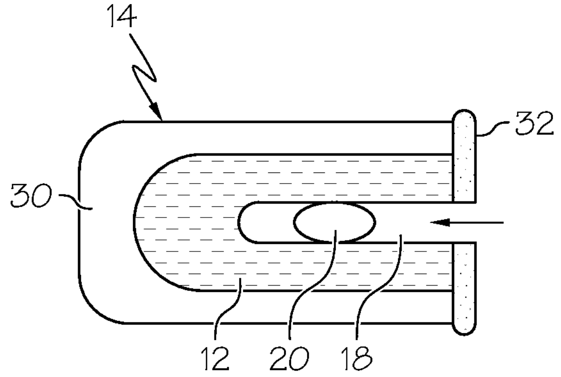
FIG. 2 is a side sectional view of the device of FIG. 1 wherein the probe element has been removed from the housing to form the recess in the edible carrier.
Figure 3:
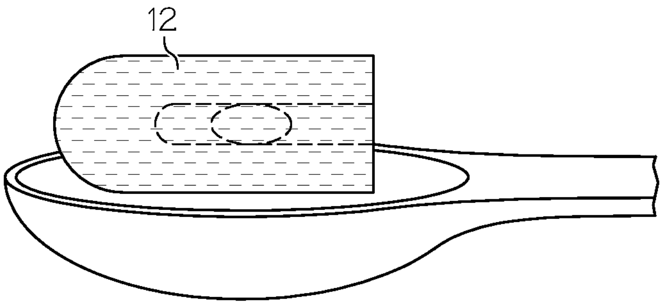
FIG. 3 shows the edible carrier placed on a spoon.
Figure 4:
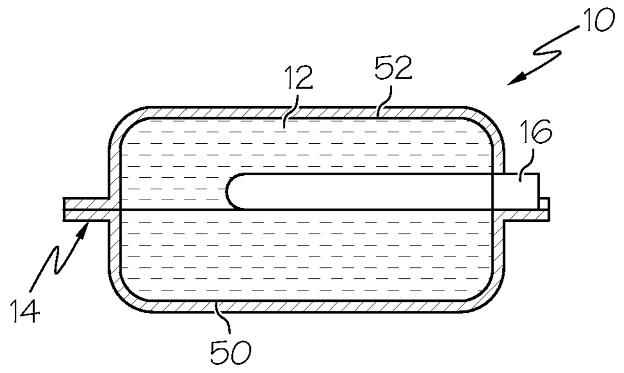
FIG. 4 is a side view of a second exemplary configuration of the device for administering medicine to a recipient.

A first exemplary configuration of the device and method is illustrated in FIGS. 1-3 wherein device 10 includes housing 14 that defines a cup-shaped base 30 that holds edible carrier 12 and a cover 32 that is releasably connected to base 30. Cup-shaped base 30 may be formed from a thin plastic material and may be vacuum formed. In this form, base 30 is deformable such that the user can crush or pinch base 30 to squeeze or push edible carrier 12 from base 30. The inner surface of base 30 may be coated with a material that helps edible carrier 12 slide from base 30.

Cover 32 may be secured to base with an adhesive. Cover 32 may be a plastic, a coated paper, or a foil. Probe element 16 extends through cover 32 into edible carrier 12. A portion of probe element 16 extends outwardly from cover 32 so that the user may grasp and twist probe element 16 about its longitudinal axis to break any connection between the material of edible carrier 12 and probe 16. The user may then pull probe element 16 straight out of housing 14 through cover 32 along the longitudinal axis of probe element 16 to define recess 18 in edible carrier 12 as depicted in FIG. 2. The user then adds medicine to recess 18 either before or after cover 32 is removed. In this condition, medicine 20 is substantially encapsulated by the material of edible carrier 12. The user then squeezes edible carrier 12 from base 30 or pushes the bottom of base 30 to eject edible carrier 12 into a spoon (FIG. 3) or the recipient's hand wherein it can be placed on the user's tongue and then swallowed. The opening of recess 18 defined by edible carrier 12 should be directed towards the front of the recipient's mouth when edible carrier 12 is placed on the tongue.

Figure 5:
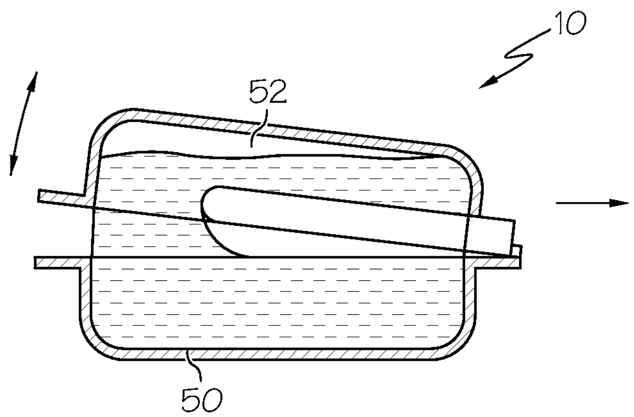
FIG. 5 is a side view showing one portion of the housing being removed from another portion of the housing.
Figure 6:
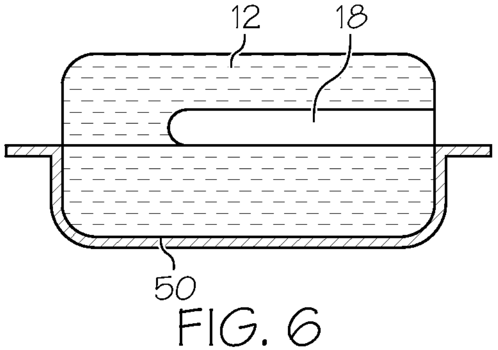
FIG. 6 is a side view of one portion of the housing supporting the edible carrier after the recess has been formed in the edible carrier.
Figure 7:
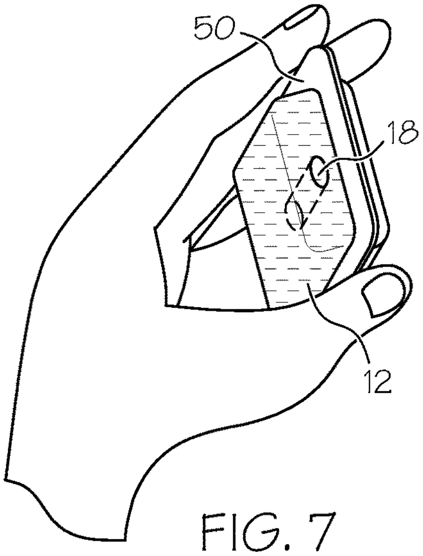
FIG. 7 shows how the edible carrier may be squeezed to open the recess so that the medicine may be inserted.
Figure 8:
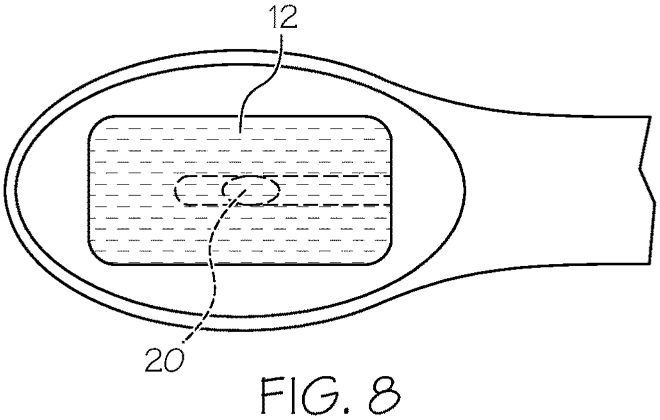
FIG. 8 depicts the edible carrier and medicine placed in a spoon for administering to the patient.

Another exemplary configuration of device 10 is depicted in FIGS. 4-8 wherein housing 14 includes at least first 50 and second 52 portions that surround edible carrier 12. Probe element 16 is connected to second portion 52 of housing 14 such that when second portion 52 of housing 14 is moved with respect to first portion 50, probe element 16 is pulled from edible carrier 12 to define recess 18 within edible carrier 12. The user may then insert medicine 20 into recess 18 and administer edible carrier 12 to the recipient. Second portion 52 may be pivoted with respect to first portion 50 as depicted in FIG. 5. Second portion 52 also may be slid or rotated with respect to first portion 50 to move probe 16 to form recess 18. Housing 14 may be formed from a release-coated thin plastic material that is readily deformable so that the user may eject edible carrier 12 from housing 14 with little effort. FIG. 7 shows how one may squeeze edible carrier 12 to open recess 18 to accept medicine 20. FIG. 8 shows the edible carrier 12 removed from first portion 50 into a spoon for delivery to the person taking the medicine. Again, the opening of recess 18 is to be positioned so that it faces the front of the mouth when delivered to the person.

Figure 9:
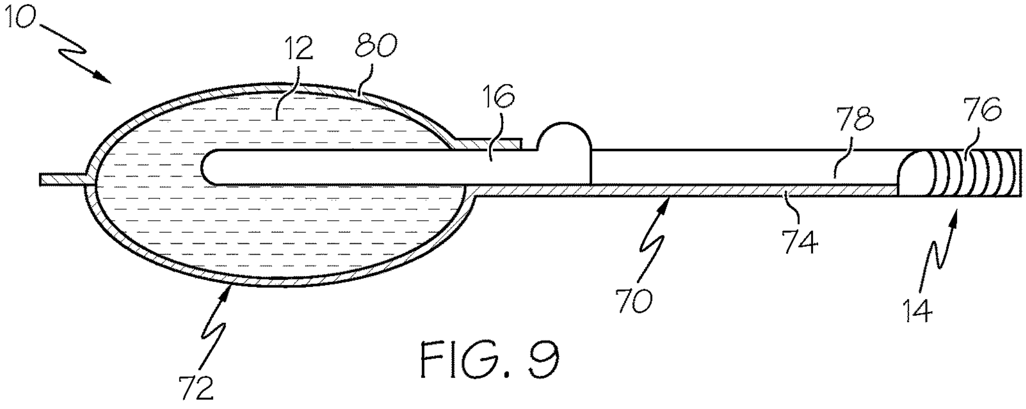
FIG. 9 is a side section view of a third exemplary configuration of the device.

A further exemplary configuration of device 10 is depicted in FIG. 9 wherein housing 14 is provided in the form of an integrated spoon such that a portion of the housing 14 itself may be used to administer edible carrier 12 and medicine 20 to the recipient. In this configuration, housing 14 is in the form of a spoon 70 with edible carrier 12 carried by the head 72 of the spoon 70. Housing 14 includes an elongated handle 74 provided with ridges 76 for gripping. Probe element 16 extends from edible carrier 12 and may be aligned with housing 14 such as the handle 74. In the exemplary configuration, handle 74 supports probe element 16 that extends from edible carrier 12. This portion of probe element 16 is seated in a groove 78 defined by handle 74 and probe element 16 may be slid back and forth within this groove 78. A seal 80 is disposed over edible carrier 12 and at least a portion of probe element 16 to protect edible carrier 12 until it is used. Seal 80 can be disposed just over the top of edible carrier 12 or disposed entirely around edible carrier 12 and spoon head 72. Seal 80 is made from any of a variety of known sealing materials such as a plastic, a foil, or a treated or coated paper.

Probe element 16 is used to form the recess in edible carrier 12 as described above. The user twists or pivots probe 16 back and forth and pulls probe element 16 back along handle groove 78 or tilts it up away from handle 74 and pulls it out of edible carrier 12. Once probe element 16 is removed, medicine 20 is placed in grove 78 and pushed into the recess defined in edible carrier 12. The end of probe element 16 may be used to push the medicine into edible carrier 12. Groove 78 helps position medicine 20 for loading into edible carrier 12.

Figure 10:
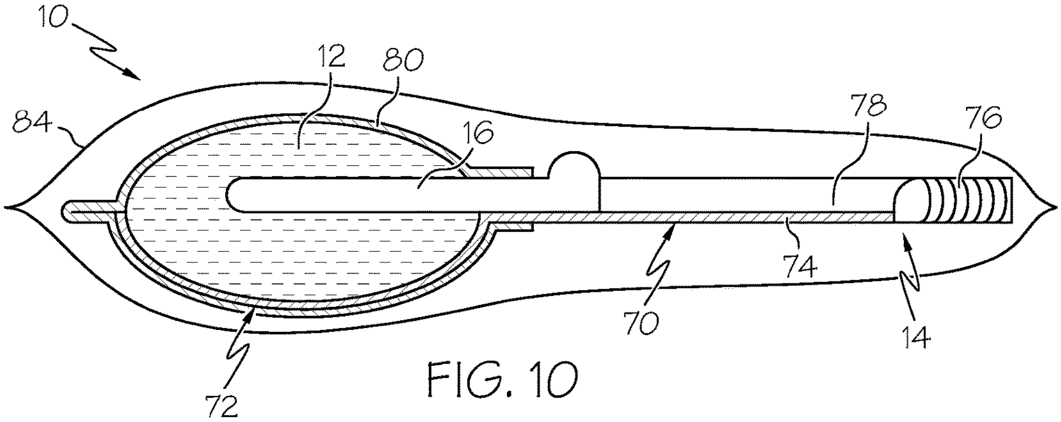
FIG. 10 is a side section view of a sealing arrangement for the third exemplary configuration of the device.
Figure 11:
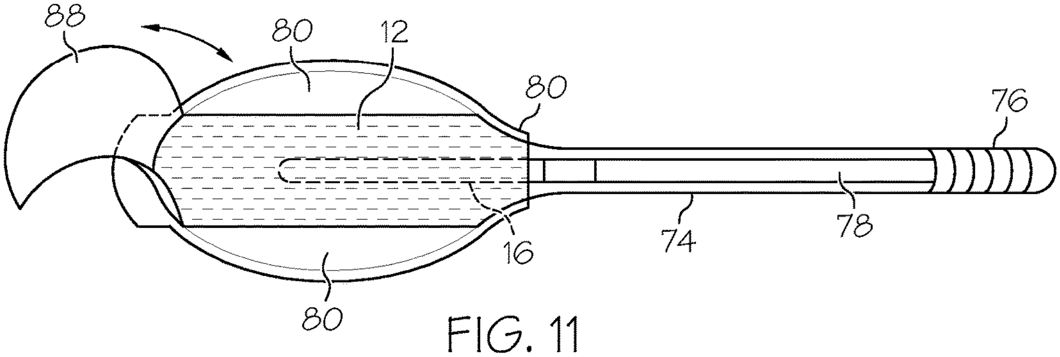
FIG. 11 is a top view of the configuration of FIG. 10.
Figure 12:
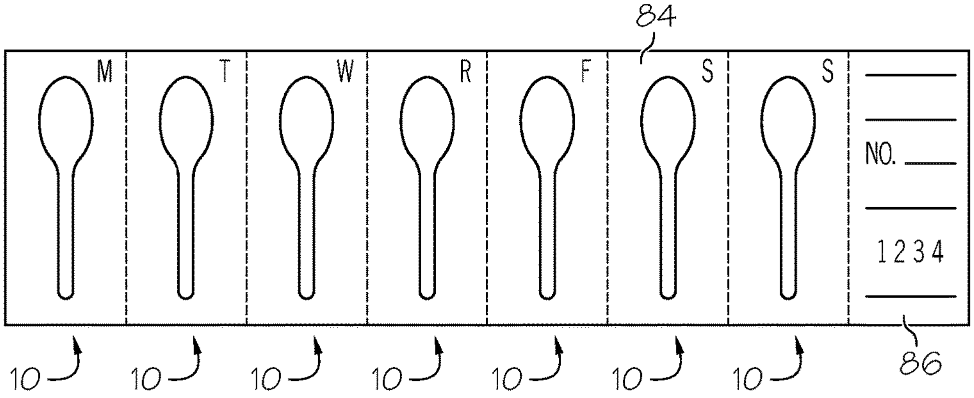
FIG. 12 is a top view of a series of devices connected together. Similar numbers refer to similar parts throughout the specification. The unnumbered views depict useful aspects of the disclosure.

FIGS. 10 and 11 depict a configuration wherein the spoon is sealed within a secondary seal 84 that protects the entire device 10 during storage and shipping. Seals 84 may be joined to form a roll or an array of devices 10 as shown in FIG. 12 wherein a roll is configured for a week. Information 86 is provided on the end of the roll and each device is labeled with a day of the week.

FIG. 11 depicts an alternative seal for the spoon head 72 wherein a tab 88 is defined by weakened areas of seal 80. Tab 88 is pulled back to provide a grip that allows the remainder of seal 80 to be removed from the spoon. The weakened areas extend from one edge to another edge of seal 80 so that seal 80 is peeled all the way across edible carrier 12 before it is used to pull the remaining portion of seal 80 off of housing 14. Tab 88 may be used with the sealing configurations of FIGS. 9 and 10.

Another configuration of housing 14 includes one wherein probe 16 is not detached from housing 14. In this example, probe 16 is disposed in edible carrier 12 until carrier 12 is removed from housing 14. When removed from housing 14, carrier 12 is slid off of probe 16 to form recess 18.

Another configuration for each of these embodiments is wherein probe 16 is hollow to allow the material that forms edible carrier 12 to be introduced to housing through probe 16.

A plurality of the devices 10 may be connected together to form a strip or array of devices 10 (shown for example in FIG. 12). These may be rolled for convenience. The individual devices 10 may be numbered with times, dates, names, room numbers, patient identification numbers, or consecutive numbering such that the user may conveniently use devices 10 with a plurality of recipients or so that a single recipient may track when the medicine has been taken. For example, devices 10 may be provided in an array of seven by three wherein the recipient needs to take medicine three times per day each day of the week.

In the foregoing description, certain terms have been used for brevity, clearness, and understanding. No unnecessary limitations are to be implied therefrom beyond the requirement of the prior art because such terms are used for descriptive purposes and are intended to be broadly construed. Moreover, the descriptions and illustrations are examples and the invention is not limited to the exact details shown or described. Throughout the description and claims of this specification the words “comprise” and “include” as well as variations of those words, such as “comprises,” “includes,” “comprising,” and “including” are not intended to exclude additives, components, integers, or steps.

The invention claimed is:

1. A device for administering medicine to a person; the device comprising:

a housing;

an edible carrier being removably carried by the housing; the edible carrier being a gelatin-based edible material that has a self-supporting body; the edible carrier adapted to provide lubrication that assists the swallowing of the medicine by the person; and a thin elongated probe element having an end embedded within and substantially surrounded by the edible carrier; the probe element being removable from the edible carrier to form a chamber extending into the edible carrier for receiving a whole, non-crushed pill or capsule that is to be administered to the person; the chamber being sized to receive the entire whole, non-crushed pill or capsule within the edible carrier.

2. The device of claim 1, further comprising a seal cooperating with the housing to cover the edible carrier.

3. The device of claim 1, wherein the housing has at least first and second portions and the probe element is connected to the second portion of the housing; the second portion of the housing being removable from the first portion of the housing to expose to the edible carrier.

4. The device of claim 1, wherein the housing has at least first and second portions with the second portion of the housing being removable from the first portion of the housing; the probe element extending through the second portion of the housing.

5. The device of claim 1, wherein the housing includes a handle.

6. The device of claim 5, wherein the probe element is carried by the handle of the housing.

7. The device of claim 6, wherein the handle defines a groove; at least a portion of the probe element being disposed in the groove defined by the handle.

8. The device of claim 7, further comprising a seal cooperating with the housing to cover the edible carrier.

9. The device of claim 8, wherein the seal defines a tab that is movable from a first position to a second position; the second position allowing the tab to function as a grip adapted to help the user remove the seal from the housing.

10. A device for administering medicine to a person; the device comprising:

a housing in the shape of a spoon having a head and a handle;

an edible carrier removably carried by the head of the spoon; the edible carrier being in the form of a gelatinous substance;

a probe element having an end embedded within and substantially surrounded by the edible carrier; the probe element being removable from the edible carrier and adapted to form a chamber extending into the edible carrier for receiving the medicine that is to be administered to the person;

the probe element being aligned with the handle of the housing; and a seal disposed over the edible carrier.

11. The device of claim 10, wherein the handle defines a groove; at least a portion of the probe element being carried within the groove defined by the handle.

12. The device of claim 11, wherein the probe element is movable from a first position within the groove of the handle to a second position within the groove of the handle.

13. The device of claim 10, wherein the seal defines a tab that is movable from a first position to a second position; the second position allowing the tab to function as a grip adapted to help the user remove the seal from the housing.

14. The device of claim 10, further comprising an outer seal surrounding the entire housing.

15. A method of administering medicine to a person; the method comprising the steps of:

providing an edible carrier carried by a housing with a probe element having an end embedded within and substantially surrounded on five sides by the edible carrier;

removing the probe element from the edible carrier to form a chamber that extends into the edible carrier;

positioning medicine to be administered to the person in the chamber of the edible carrier; and placing the edible carrier with the medicine in the chamber in the person's mouth.

16. The method of claim 15, further comprising the steps of placing the medicine to be administered in a groove defined by the housing before the medicine is positioned in the chamber of the edible carrier.

17. The method of claim 16, wherein the step of positioning medicine includes the step of pushing the medicine along the groove of the housing into the chamber.

18. The method of claim 17, further comprising the step of pushing the medicine with the probe element.

19. The method of claim 15, wherein the chamber formed in the edible carrier has an opening and further comprising the steps of locating the edible carrier in the head of a spoon before the edible carrier is placed in the person's mouth and positioning the opening of the chamber toward a handle portion of the spoon.

20. The method of claim 15, further comprising the steps of providing the edible carrier with a seal that has a tab, moving the tab from a first position to a second position, and using the tab to remove the seal from the edible carrier.

* * * * *